United States Patent [19]

Conrow et al.

[11] 4,159,384

[45] Jun. 26, 1979

[54] PHENENYLTRIS (CARBONYLIMINO)MULTI-ANIONIC SUBSTITUTED TRIPHENYL ACIDS AND SALTS

[75] Inventors: Ransom B. Conrow, Pearl River; Seymour Bernstein, New City, both of N.Y.

[73] Assignee: American Cyanamid Company, Stamford, Conn.

[21] Appl. No.: 938,996

[22] Filed: Sep. 1, 1978

Related U.S. Application Data

[62] Division of Ser. No. 805,773, Jun. 13, 1977, Pat. No. 4,123,455.

[51] Int. Cl.$^2$ .................. C07C 101/48; A61K 31/24

[52] U.S. Cl. .................................................. 560/46
[58] Field of Search .................. 560/46, 48, 138; 260/507 R; 562/453, 457

[56] References Cited

U.S. PATENT DOCUMENTS

| 4,118,585 | 10/1978 | Conrow et al. ............... 562/457 |
| 4,120,895 | 10/1978 | Conrow et al. ............... 562/457 |

*Primary Examiner*—Bernard Helfin
*Assistant Examiner*—G. T. Breitenstein
*Attorney, Agent, or Firm*—Claude J. Caroli

[57] ABSTRACT

Phenenyltris(carbonylimino) multi-anionic substituted triphenyl acids and salts useful as complement inhibitors.

20 Claims, No Drawings

PHENENYLTRIS(CARBONYLIMINO)MULTI-ANIONIC SUBSTITUTED TRIPHENYL ACIDS AND SALTS

This is a division of application Ser. No. 805,773, filed June 13, 1977, now U.S. Pat. No. 4,123,455.

DESCRIPTION OF THE INVENTION

This invention is concerned with compounds of the formula:

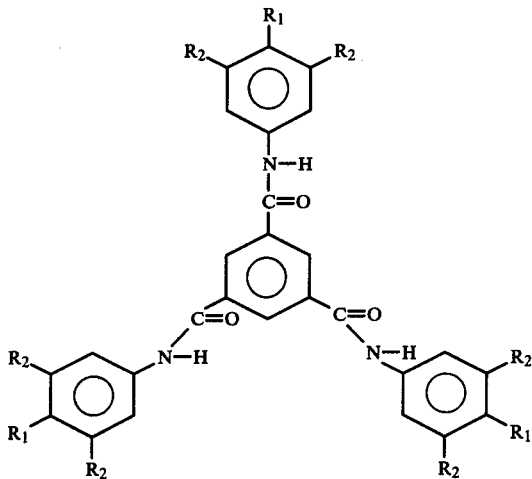

wherein $R_1$ is selected from the group consisting of hydrogen, hydroxy, acetyloxy and $COOR_3$, wherein $R_3$ is selected from the group consisting of alkali metal and alkali earth metal; and $R_2$ is selected from the group consisting of hydrogen, methyl, $SO_3R_3$, wherein $R_3$ is as previously defined, and $COOR_4$ wherein $R_4$ is selected from the group consisting of hydrogen, methyl, alkali metal and alkali earth metal; and the pharmaceutically acceptable salts thereof.

A preferred embodiment of the invention consists of those compounds wherein $R_1$ is selected from the group consisting of hydrogen, hydroxy and acetyloxy; and $R_2$ is as previously defined.

A second preferred embodiment consists of those compounds wherein $R_1$ is selected from the group consisting of $COOR_3$, wherein $R_3$ is as previously defined; and $R_2$ is as previously defined.

A most preferred embodiment of the first preferred embodiment consists of those compounds wherein $R_1$ is selected from the group consisting of hydrogen and hydroxy; and $R_2$ is selected from the group consisting of $COOR_4$ and $SO_3R_3$, wherein $R_3$ and $R_4$ are as previously defined.

A most preferred embodiment of the second preferred embodiment consists of those compounds wherein $R_1$ is as previously defined; and $R_2$ is selected from the group consisting of $COOR_4$, wherein $R_4$ is as previously defined.

The compounds of the present invention may be prepared by reacting 1,3,5-benzenetricarboxylic acid chloride with an appropriate amine containing compound in a basic medium for a period of several hours. The desired product is derived by conventional extraction procedures. See Flowsheet A.

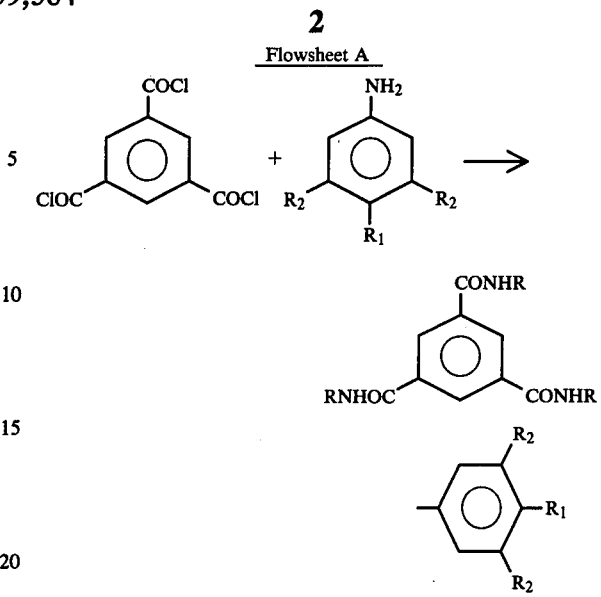

wherein R is selected from the group comprising and $R_1$ and $R_2$ are as herein above described.

In addition, compounds wherein $R_1$ and/or $R_2$ are esters may be hydrolyzed by conversion to the sodium salt which may be converted to the carboxylic acid in mineral acid.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C2s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39, 935–938 (1968); Ann. Rev. Medicine, 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, Oct. 11, 1974, pp. 53–58; 64–66; J. Allergy Clin. Immunol., 53, 298–302 (1974); Cold Spring Harbor Conf. Cell Proliferation 2/Proteases Biol. Control/229–241 (1975); Annals of Internal Medicine, 84, 580–593 (1976); "Complement: Mechanisms and Functions", Prentice-Hall, Englewood Cliffs, N.J. (1976).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) and attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327–339 (1952). The compound 8-(3-benzamido-4-methylbenzamido)naphthalene-1,3,5-trisulfonic acid (Suramin) is described as a competitive inhibitor of the complement system, Clin. Exp. Immunol., 10, 127–138 (1972). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 93, 629–640 (1964); The Journal of Immunology, 104, 279–288 (1970); The Journal of Immunology, 106, 241–245 (1971); and the Journal of Immunology, 111, 1061–1066 (1973).

It has been reported that the known complement inhibitors epsilon-aminocaproic acid, Suramin and tranexamic acid all have been used with success in the treatment of hereditary angioneurotic edema, a disease state resulting from an inherited deficiency or lack of function of the serum inhibitor of the activated first compliment of complement (C1 inhibitor), The New England Journal of Medicine, 286, 808–812 (1972). It has also been reported that the drug, pentosan-poly-sulfoester, has an anticomplementary activity on human serum both in vitro and in vivo, as judged by a reduction in total hemolytic complement activity; Pathologie Biologie, 25, 33–36 (1977).

SPECIFIC DISCLOSURE

EXAMPLE 1

5,5',5''-[s-Phenenyltris(carbonylimino)]tri-isophthalic acid hexamethyl ester

A mixture of 52.8 g of 5-nitroisophthalic acid in 500 ml of absolute methanol containing 10 ml of sulfuric acid is refluxed for 15 hours. The mixture is cooled and filtered giving 50 g of 5-nitrodimethyl isophthalate.

The above material in 350 ml of dimethylformamide containing 4.0 g of palladium on carbon catalyst is hydrogenated in Parr shaker for 30 minutes and then filtered through diatomaceous earth. The filtrate is poured into 1500 ml of water and filtered. The solid is washed with water, air dried, dissolved in 750 ml of refluxing ethanol, treated with charcoal and filtered through diatomaceous earth. The filtrate is concentrated to give pale yellow crystals of 5-aminodimethyl isophthalate.

To a warm solution of 2.09 g of this amino derivative in 30 ml of 1:1 pyridine:acetonitrile is added a solution of 885 mg of 1,3,5-benzenetricarboxylic acid chloride in 5 ml of acetonitrile giving an immediate precipitate. The mixture is diluted with 100 ml of water and filtered. The solid is washed with water, dried, recrystallized from 20 ml of dimethylsulfoxide and dried at 110° C. to give the desired product as colorless crystals, mp 345°–355° C.

EXAMPLE 2

5,5',5''-[s-Phenenyltris(carbonylimino)]tri-isophthalic acid hexasodium salt

A solution of 21.1 g of 5-nitroisophthalic acid in a mixture of 110 ml of water and 40 ml of 5 N sodium hydroxide is neutralized with 0.3 ml of acetic acid and then hydrogenated with 2.0 g of palladium on carbon in a Parr shaker for 1.5 hours. The mixture is filtered and to the filtrate, which contains 5-amino isophthalic acid disodium salt, is added 15 g of sodium acetate trihydrate followed by 8.85 g of finely ground 1,3,5-benzenetricarboxylic acid chloride. The mixture is stirred vigorously while being cooled in a water bath for 30 minutes. An 8.5 g portion of sodium bicarbonate is added and stirring is continued for 6 hours. The mixture is filtered and the gel-like precipitate is washed with water, ethanol and finally ether giving a colorless powder.

A 12.8 g portion of this powder is suspended in 100 ml of water and made basic with 10 ml of 5 N sodium hydroxide. The mixture is warmed to produce a solution, neutralized with acetic acid and filtered. The filtrate is warmed on a steam bath and diluted with 50 ml of ethanol. Standing overnight produces a colorless precipitate which is recovered by filtration and washed with 2:1 water:ethanol, ethanol and finally ether giving a colorless powder. This powder is dissolved in 80 ml of warm water and made weakly basic with 5 N sodium hydroxide. An 80 ml portion of ethanol is added and after standing overnight the mixture is filtered giving the desired product as a pale yellow powder, mp>350° C.

EXAMPLE 3

5,5′,5″-[s-Phenenyltris(carbonylimino)]tri-salicyclic acid trimethyl ester

A solution of 10 g of 5-aminosalicyclic acid, 100 ml of methanol and 5 ml of sulfuric acid are refluxed overnight. The reaction mixture is cooled, basified with sodium carbonate and the methanol is evaporated. The resulting solid is washed with water and dried giving 4.0 g of methyl-5-aminosalicylic acid.

To a solution of 2.0 g of the above product and 946 mg of pyridine in 10 ml of acetonitrile at room temperature, is added 1.06 g of 1,3,5-benzenetricarboxylic acid. The mixture is stirred for 48 hours, acidified with dilute hydrochloric acid and filtered. The solid is washed with dilute HCl and water and dried giving the desired product as a light grey solid, mp 283°-286° C.

EXAMPLE 4

5,5′,5″-[s-Phenenyltris(carbonylimino)]tri-3-sulfo salicylic acid trisodium salt To a solution of 4.7 g of 5-amino-2-hydroxy-3-sulfobenzoic acid in 100 ml of water containing 6.4 g of sodium carbonate is added 1.76 g of 1,3,5-benzenetricarboxylic acid chloride dissolved in a minimum of acetonitrile. The mixture is stirred for 48 hours and then treated essentially as described in Example 3 giving the desired product as a grey powder.

EXAMPLE 5

5,5′,5″-[s-Phenenyltris(carbonylimino)]tri-salicylic acid trimethyl ester, triacetate A mixture of 500 mg of 5,5′,5″-[s-phenenyltris(carbonylimino)]tri-salicylic acid trimethyl ester, 8 ml of acetic anhydride and 3 drops of sulfuric acid is stirred at room temperature overnight. The mixture is poured into ice, stirred for 30 minutes and then filtered. The gummy solid is washed with water, combined with ethanol and evaporated in vacuo giving the desired product as a light grey powder, mp 248°-254° C.

EXAMPLE 6

5,5′,5″-[s-Phenenyltris(carbonylimino)]tri-2,3-cresotic acid trimethyl ester

A solution of 3.0 g of 3-methyl-5-nitrosalicylic acid methyl ester and 300 mg of 10% palladium on carbon in 200 ml of ethanol is hydrogenated in a Parr shaker, filtered through diatomaceous earth and evaporated to dryness. The residue is recrystallized from ethyl acetate-hexane giving 1.85 g of 5-amino-3-methyl salicylic acid methyl ester.

To a solution of 837 mg of the above product in 9 ml of acetonitrile and 366 mg of pyridine is slowly added 385 mg of 1,3,5-benzenetricarboxylic acid chloride in one ml of acetonitrile. The reaction proceeds essentially as described in Example 3 giving the desired product, mp 288°-292° C.

EXAMPLE 7

5,5′,5″-[s-Phenenyltris(carbonylimino)]tri-salicylic acid

To a solution of 6.1 g of 5-aminosalicylic acid and 8.5 g of sodium carbonate in 100 ml of water is added slowly 2.65 g of 1,3,5-benzenetricarboxylic acid chloride in a minimum amount of acetonitrile. The reaction proceeds essentially as described in Example 3 giving the desired product, mp 280°-286° C.

EXAMPLE 8

5,5′,5″-[s-Phenenyltris(carbonylimino)]tri-2,3-cresotic acid

A solution of 820 mg of 5,5′,5″-[s-Phenenyltris(carbonylimino)]tri-2,3-cresotic acid trimethyl ester and 7 ml of 1 N sodium hydroxide is stirred at room temperature for 5 hours. The mixture is acidified with dilute hydrochloric acid, stirred for one hour and then filtered. The solid is washed with water and dried giving the desired product as a brown solid, mp 301°-314° C.

EXAMPLE 9

5,5′,5″-[s-Phenenyltris(carbonylimino)]tri-isophthalic acid hexamethyl ester

A mixture of 40 ml of sulfuric acid and 33 ml of nitric acid is stirred for 10 minutes and then 10 ml of acetic acid is added. To this is added a suspension of 10 g of 2-hydroxyisophthalic acid (Org. Syn., Vol. 5, p. 617) in 20 ml of acetic acid slowly with cooling in a water bath. A 10 ml portion of acetic acid is added. The reaction mixture is dissolved in water and extracted with ether. The ether is washed with saturated saline, dried over sodium sulfate and evaporated giving 5-nitro-2-hydroxyisophthalic acid as an orange oil.

The above product is refluxed in a mixture of 250 ml of methanol and 10 ml of sulfuric acid. The reaction mixture is cooled and then concentrated in vacuo. The solid is collected, washed with water and petroleum ether and air dried. One recrystallization gives 2.84 g of crystals of 5-nitro-2-hydroxyixophthalic acid methyl ester.

A solution of 2.0 g of the above nitro ester and 200 mg of 10% palladium on carbon in 200 ml of ethyl acetate is reduced in Parr shaker giving 1.04 g of 5-amino-2-hydroxyisophthalic acid methyl ester.

A 1.04 g portion of the above amine, 9 ml of acetonitrile, 366 mg of pyridine and 385 mg of 1,3,5-benzenetricarboxylic acid chloride in acetonitrile is reacted essentially as described in Example 3 giving the desired product as a solid, mp 297°-311° C.

EXAMPLE 10

5,5′,5″-[s-Phenenyltris(carbonylimino)]tri-salicylic acid triacetate

A solution of 150 mg of 5,5′,5″-[s-phenenyltris(carbonylimino)]tri-salicylic acid in 5 ml of acetic acid, 5 ml of acetic anhydride and 5 drops of sulfuric acid is stirred. Water is added, the mixture is filtered and the solid is washed with water and dried with ethanol, giving the desired product as a solid, mp>350° C.

EXAMPLE 11

5,5′,5″-[s-Phenenyltris(carbonylimino)]tri-2-hydroxyisophthalic acid

A mixture of 200 mg of 5,5′,5″-[s-phenenyltris(carbonylimino)]tri-isophthalic acid hexamethyl ester, 10 ml of pyridine and 294 mg of lithium iodide trihydrate is refluxed overnight. The reaction mixture is cooled, acidified to pH2 with dilute hydrochloric acid and filtered. The solid is washed with water and dried with ethanol, giving the desired product, mp>350° C.

EXAMPLE 12

4,4′,4″-[s-Phenenyltris(carbonylimino)]tri-phthalic acid hexasodium salt

A 2.5 g portion of 4-aminophthalic acid in 100 ml of water is neutralized to pH 7.2 with sodium hydroxide. A 1.47 g portion of sodium carbonate is added. To this is added a solution of 1.21 g of 1,3,5-benzenetricarboxylic acid chloride in 15 ml of ether, dropwise with vigorous stirring. Stirring is continued for 18 hours and then the mixture is concentrated to 40 ml and acidified with hydrochloric acid. The solid is collected, washed with ethanol and ether, dried and then dissolved in 25 ml of water. After neutralizing with base, 25 ml of ethanol is added, the mixture is heated to give a solution and then allowed to cool. The solid is collected, washed with ethanol and ether and dried giving the desired product.

EXAMPLE 13

4,4′,4″-[s-Phenenyltris(carbonylimino)]tri-2-sulfobenzoic acid hexasodium salt

To a solution of 3.6 g of 4-amino, 2-sulfobenzoic acid, disodium salt and 1.47 g of sodium carbonate in 40 ml of water is added a solution of 1.21 g of 1,3,5-benzenetricarboxylic acid chloride in 15 ml of ether. The mixture is stirred for 48 hours, filtered and then concentrated. The residue is dissolved in 30 ml of hot water and 30 ml of ethanol, stirred for one hour, filtered and the solid is washed with 50% aqueous ethanol, ethanol and then ether. The solid is dissolved in 30 ml of water, adjusted to pH 2 with hydrochloric acid, precipitated with ethanol, washed with ethanol and ether and dried. This solid is dissolved in 30 ml of water, adjusted to pH 7.2 and 25 ml of ethanol is added. The mixture is stirred overnight, filtered, washed and dried giving the desired product. The filtrate contains additional product which may be extracted with ethanol.

EXAMPLE 14

4,4′,4″-[s-Phenenyltris(carbonylimino)]tri-benzoic acid trisodium salt

To a solution of 6.16 g of 4-aminobenzoic acid and 3.62 ml of pyridine in 80 ml of acetone is added 3.98 g of 1,3,5-benzenetricarboxylic acid chloride. The mixture is stirred for 30 minutes, filtered and the solid is washed with acetone, water, acetone and finally ether. This solid is slurried in 100 ml of water and sodium hydroxide is added to produce solution. The solution is filtered and the filtrate is treated with ethanol giving the desired product as a solid.

EXAMPLE 15

3,3′,3″-[s-Phenenyltris(carbonylimino)]tri-benzoic acid trisodium salt

A 5.5 g portion of 2-metanilic acid in 100 ml of water is neutralized to pH 7.2. A 4.25 g portion of sodium carbonate is added. A 2.65 g portion of 1,3,5-benzenetricarboxylic acid chloride in 20 ml of ether is added and the mixture is stirred overnight. The solution is acidified to pH 1, filtered and the solid is washed with water. The solid is reslurried in water, acidified to pH 1, filtered and the solid is washed with water, ethanol and then ether. Further treatment with ethanol gives the desired product.

EXAMPLE 16

5,5′,5″-[s-Phenenyltris(carbonylimino)]tri-m-benzenedisulfonic acid hexasodium salt A 3.98 g portion of 5-amino-1,3-benzenedisulfonic acid disodium salt and 1.47 g of sodium carbonate are dissolved in 50 ml of water. A 1.21 g portion of 1,3,5-benzenetricarboxylic acid chloride is added with vigorous stirring. Stirring is continued for 5 hours and the solution is treated essentially as described in Example 15 giving the desired product.

EXAMPLE 17

Preparation of Compressed Tablet

| Ingredient | mg/Tablet |
| --- | --- |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 18

Preparation of Compressed Tablet—Sustained Action

| Ingredient | mg/Tablet |
| --- | --- |
| Active Compound as Aluminum Lake*, Micronized | 0.5–500(as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 19

Preparation of Hard Shell Capsule

| Ingredient | mg/Capsule |
| --- | --- |
| Active Compound | 0.5–500 |
| Lactose, Spray Dried | qs |
| Magnesium Stearate | 1–10 |

EXAMPLE 20

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 21

Preparation of Oral Liquid (Elixir)

| Ingredient | % W/V |
| --- | --- |
| Active Compound | 0.05–5 |

-continued

| Ingredient | % W/V |
|---|---|
| Alcohol USP | 12.5 |
| Glycerin USP | 45.0 |
| Syrup USP | 20.0 |
| Flavoring Agent | qs |
| Purified Water qs ad | 100.0 |

EXAMPLE 22

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs. ad | 100.0 |

EXAMPLE 23

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 24

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 25

Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 26

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |

-continued

| Ingredient | % W/V |
|---|---|
| Water for Injection qs ad | 100.0 |

The compounds of the present invention may be administered internally, e.g., orally, intra-articularly or parenterally, e.g., intra-articular, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore as well as the sodium salt, those of the alkali metals, such as potassium and lithium; of ammonia; and of the alkaline earth metals, such as calcium or magnesium, may be employed. It will be apparent, therefore, that these salts embrace, in general derivatives of salt-forming cations.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures or polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such as active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test, Code 035 (C3-C9 inhibitor)—This test determines the ability of the late components of human complement (C3-C9) to lyse EAC 142 in the presence of appropriate dilutions of the test compound. An active inhibitor protects EAC 142 from lysis by human C3-C9; (iii) Test, Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7-8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036, Cap 50, % inhibition and Forssman shock. Table I shows that the compounds of the invention possess highly significant in vitro and in vivo, complement inhibiting activity in warm-blooded animals.

TABLE I

| | Biological Activities | | | |
|---|---|---|---|---|
| Compound | C1 026* Wells | C-Late 035* Wells | Shunt Inhibition 036* Wells | Cap 50* |
| 5,5',5''-[s-Phenenyltris(carbonylimino)]tri-isophthalic acid hexasodium salt | +3, +4 | | | >500 |
| 5,5',5''-[s-Phenenyltris(carbonylimino)]tri-3-sulfo salicylic acid trisodium salt | +5, +4 | | +1 | 235 |
| 5,5',5''-[s-Phenenyltris(carbonylimino)]tri-salicylic acid | +2, +4 | +1, +4 | | |
| 5,5',5''-[s-Phenenyltris(carbonylimino)]tri-2,3-cresotic acid | +2, +4 | | | |
| 5,5',5''-[s-Phenenyltris(carbonylimino)]tri-salicylic acid triacetate | +1, +4 | | | |
| 5,5',5''-[s-Phenenyltris(carbonylimino)]tri-2-hydroxy isophthalic acid | +3, +4 | | | |

TABLE I-continued

| | Biological Activities | | | |
|---|---|---|---|---|
| Compound | Cl 026* Wells | C-Late 035* Wells | Shunt Inhibition 036* Wells | Cap 50* |
| 4,4′,4″-[s-Phenenyltris(carbonylimino)]tri-phthalic acid hexasodium salt | +2, +5 | | | |
| 5,5′,5″-[s-Phenenyltris(carbonylimino)]tri-m-benzenedisulfonic acid hexasodium salt | +4, +4 | | 430 | |

*Code designations for tests employed as referred to herein.

We claim:

1. A compound of the formula:

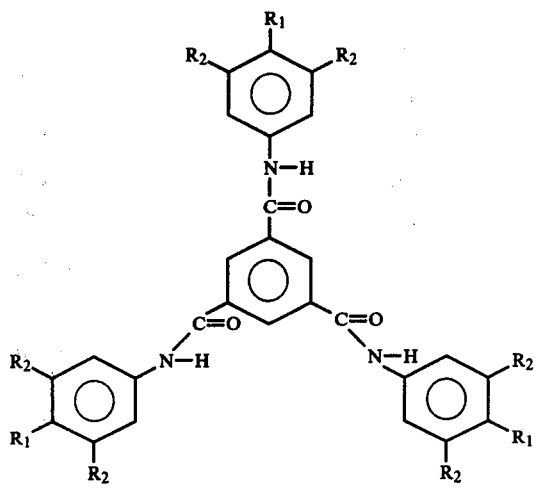

wherein $R_1$ is selected from the group consisting of hydrogen, hydroxy, acetyloxy and $COOR_3$, wherein $R_3$ is selected from the group consisting of alkali metal and alkali earth metal; and $R_2$ is selected from the group consisting of hydrogen, methyl, $SO_3R_3$, wherein $R_3$ is as previously defined, and $COOR_4$, wherein $R_4$ is selected from the group consisting of hydrogen, methyl, alkali metal and alkali earth metal; and the pharmaceutically acceptable salts thereof; with the proviso that when $R_1$ is hydrogen, $R_2$ is not $SO_3R_3$.

2. A compound according to claim 1, wherein $R_1$ is selected from the group consisting of hydrogen, hydroxy and acetyloxy; and $R_2$ is as previously defined.

3. A compound according to claim 1, wherein $R_1$ is selected from the group consisting of $COOR_3$, wherein $R_3$ is as previously defined; and $R_2$ is as previously defined.

4. A compound according to claim 2, wherein $R_1$ is selected from the group consisting of hydrogen and hydroxy; and $R_2$ is selected from the group consisting of $COOR_4$ and $SO_3R_3$, wherein $R_3$ and $R_4$ are as previously defined.

5. A compound according to claim 3, wherein $R_1$ is as previously defined; and $R_2$ is selected from the group consisting of $COOR_4$, wherein $R_4$ is as previously defined.

6. The compound according to claim 1, 5,5′,5″-[s-Phenenyltris(carbonylimino)]tri-isophthalic acid hexamethyl ester.

7. The compound according to claim 1, 5,5′,5″-[s-Phenenyltris(carbonylimino)]tri-isophthalic acid hexasodium salt.

8. The compound according to claim 1, 5,5′,5″,-[s-Phenenyltris(carbonylimino)]tri-salicylic acid trimethyl ester.

9. The compound according to claim 1, 5,5′,5″-[s-Phenenyltris(carbonylimino)]tri-3-sulfo salicylic acid tri-sodium salt.

10. The compound according to claim 1, 5,5′,5″-[s-Phenenyltris(carbonylimino)]tri-salicylic acid trimethyl ester, triacetate.

11. The compound according to claim 1, 5,5′,5″-[s-Phenenyltris(caarbonylimino)]tri-2,3-cresotic acid trimethyl ester.

12. The compound according to claim 1, 5,5′,5″-[s-Phenenyltris(carbonylimino)]tri-salicylic acid.

13. The compound according to claim 1, 5,5′,5″-[s-Phenenyltris(carbonylimino)]tri-2,3-cresotic acid.

14. The compound according to claim 1, 5,5′,5″-[s-Phenenyltris(carbonylimino)]tri-isophthalic acid hexamethyl ester.

15. The compound according to claim 1, 5,5′,5″-[s-Phenenyltris(carbonylimino)]tri-salicylic acid triacetate.

16. The compound according to claim 1, 5,5′,5″-[s-Phenenyltris(carbonylimino)]tri-2-hydroxy-isophthalic acid.

17. The compound according to claim 1, 4,4′,4″-[s-Phenenyltris(carbonylimino)]tri-phthalic acid hexasodium salt.

18. The compound according to claim 1, 4,4′,4″-[s-Phenenyltris(carbonylimino)]tri-2-sulfobenzoic acid hexasodium salt.

19. The compound according to claim 1, 4,4′,4″-[s-Phenenyltris(carbonylimino)]tri-benzoic acid trisodium salt.

20. The compound according to claim 1, 3,3′,3″-[s-Phenenyltris(carbonylimino)]tri-benzoic acid trisodium salt.

* * * * *